US012672987B2

(12) United States Patent
Michiels et al.

(10) Patent No.: US 12,672,987 B2
(45) Date of Patent: Jul. 7, 2026

(54) MULTI-LAYERED NON-WOVEN STRUCTURE FOR USE AS A COMPONENT OF DISPOSABLE ABSORBENT ARTICLES

(71) Applicant: TWE MEULEBEKE, Meulebeke (BE)

(72) Inventors: Dany Michiels, Haaltert (BE);
Véronique Decambray, Waregem (BE)

(73) Assignee: TWE MEULEBEKE, Meulebeke (BE)

( * ) Notice: Subject to any disclaimer, the term of this patent is extended or adjusted under 35 U.S.C. 154(b) by 873 days.

(21) Appl. No.: 17/260,800

(22) PCT Filed: Jul. 19, 2018

(86) PCT No.: PCT/EP2018/069599
§ 371 (c)(1),
(2) Date: Jan. 15, 2021

(87) PCT Pub. No.: WO2020/015829
PCT Pub. Date: Jan. 23, 2020

(65) Prior Publication Data
US 2021/0322232 A1 Oct. 21, 2021

(51) Int. Cl.
*A61F 13/513* (2006.01)
*A61F 13/15* (2006.01)
(Continued)

(52) U.S. Cl.
CPC .. *A61F 13/51311* (2013.01); *A61F 13/15731* (2013.01); *A61F 13/15739* (2013.01);
(Continued)

(58) Field of Classification Search
CPC .......... A61F 13/51311; A61F 13/51305; A61F 13/513; A61F 13/53; A61F 2013/530481;
(Continued)

(56) References Cited

U.S. PATENT DOCUMENTS 4,102,340 A * 7/1978 Mesek .............. A61F 13/53743
604/377
4,994,037 A * 2/1991 Bernardin ......... A61F 13/51121
604/378
(Continued)

FOREIGN PATENT DOCUMENTS

BE 1018052 A3 4/2010
CN 107109731 A 8/2017
(Continued)

*Primary Examiner* — Jacqueline F Stephens
*Assistant Examiner* — Seth Han
(74) *Attorney, Agent, or Firm* — Maschoff Brennan

(57) ABSTRACT

The present invention relates to multi-layered non-woven structures being useful as components of disposable absorbent articles and garments comprising super absorbent particles and thereby acts as a core. The invention thereby ensures that the body fluids can penetrate from a first layer, which acts as an acquisition layer, up to a third layer comprising SAP particles, the second non-woven layer serving to decrease the fluid volume per surface unit, as a conventional dispersion layer. However the second layer of the invention additionally acts like a non-return valve, preventing, or at least strongly limiting, any fluid transfer from the third layer to the first layer. Channels free of SAP can additionally be design to improve the inlet and rewet properties of the multilayer acquisition and distribution sheet non-woven material.

4 Claims, 10 Drawing Sheets

(51) Int. Cl.

| | |
|---|---|
| *A61F 13/51* | (2006.01) |
| *A61F 13/512* | (2006.01) |
| *A61F 13/53* | (2006.01) |
| *D06N 3/00* | (2006.01) |

(52) U.S. Cl.
CPC ........ *A61F 13/5125* (2013.01); *D06N 3/0011* (2013.01); *D06N 3/0059* (2013.01); *D06N 3/0068* (2013.01); *A61F 2013/51066* (2013.01); *A61F 2013/51372* (2013.01); *A61F 2013/530481* (2013.01); *D06N 2209/126* (2013.01); *D06N 2211/24* (2013.01)

(58) Field of Classification Search
CPC .............. A61F 13/537; A61F 13/53708; A61F 13/53713; A61F 13/53717; A61F 13/532; A61F 13/15642; A61F 13/1565; A61F 2013/5307; A61F 13/535; A61F 2013/15447
See application file for complete search history.

(56) References Cited

U.S. PATENT DOCUMENTS

| | | | | |
|---|---|---|---|---|
| 6,511,566 B1 * | 1/2003 | Wessel | ............. | A61F 13/53747 156/73.2 |
| 6,703,330 B1 * | 3/2004 | Marsh | ..................... | D04H 1/44 604/387 |
| 2005/0054255 A1 * | 3/2005 | Morman | .......... | A61F 13/51121 442/381 |
| 2015/0065974 A1 * | 3/2015 | Michiels | ................ | B32B 37/12 156/73.6 |
| 2020/0060894 A1 * | 2/2020 | Suyama | ........... | A61F 13/53409 |

FOREIGN PATENT DOCUMENTS

| | | | | |
|---|---|---|---|---|
| WO | 03061524 A2 | 7/2003 | | |
| WO | 2013152809 A1 | 10/2013 | | |
| WO | WO-2013187375 A1 * | 12/2013 | ............. | A61F 13/53 |
| WO | 2014093323 A1 | 6/2014 | | |
| WO | 2016/108039 A1 | 7/2016 | | |
| WO | 2017087155 A1 | 5/2017 | | |

* cited by examiner

1

MULTI-LAYERED NON-WOVEN STRUCTURE FOR USE AS A COMPONENT OF DISPOSABLE ABSORBENT ARTICLES

FIELD OF THE INVENTION

The present invention relates to multi-layered non-woven structures being useful as components of disposable absorbent articles and garments comprising super absorbent particles. The invention also relates to the disposable absorbent articles or garments comprising said multi-layered non-woven structures, such as sanitary napkins, panty liners, baby diapers, adult incontinence pads, feminine hygiene products, training pants, sweat pads, medical wound bandages and the like. The invention also relates to a process for making said multi-layered non-woven structures.

BACKGROUND OF THE INVENTION

The main elements of a conventional disposable absorbent article or garment, referring to the attached FIG. 1, include a liquid permeable or pervious, preferably hydrophilic, outer layer 11 (usually referred to as the top-sheet), an acquisition and distribution layer 12 (usually referred to as ADL), a liquid impermeable or impervious outer layer 14 (usually referred to as the back-sheet) and an absorbent core 13 sandwiched between the ADL 12 and the back-sheet. Absorbent cores 13 are generally composed of fluff usually made of fibers having a swelling potential like cellulose. To increase the absorbing capacity of the fluff, super absorbent polymer (SAP) particles, i.e. polymer particles capable of absorbing huge amounts (preferably from 10 to 1000 times their own weight) of an aqueous liquid, such as urine, blood or both, are spread within the fluff.

The ADL comprises generally an acquisition layer, which is suitable to rapidly acquire the liquid influx coming onto a limited area of this layer, and transmits it to at least one distribution layer, allowing the liquid to migrate away from the body of the garment user and spread over a larger area of the layer, thereby lowering the liquid flow rate per surface unit.

An acquisition and distribution layer (ADL) system is disclosed for instance in patent BE 1 018 052. Acquisition layers are generally composed of coarse fibers that quickly transmit the liquid by capillarity to the dispersion layer. Said dispersion layer generally comprise hydrophilic material and fibers suitable in hygiene articles.

Typical SAP particles are composed of cross-linked hydrophilic polymer chains. Hydrophilic polymers are either natural or synthetic polymers or a mixture of both types. Common natural polymers include cellulose-based polymer such as cellulose or starch eventually modified by additional hydrophilic functions for example carboxylate, phosphonate or sulfoxylate. Synthetic superabsorbent hydrophilic polymers usually are acrylic based polymers. SAP particles may be at least partially coated. The additional coating improves or provides additional properties to the SAP particles such as a better body fluid absorbing and retention capacity, a better adhesion of the particles to the surrounding or better mechanical properties.

An absorbent core generally comprises a mixture of SAP particles and a substrate, such as fibers, fluff or any combination thereof. When the absorbent core is wetted by a body fluid, the SAP particles are able to absorb a large amount of liquid. However, wet SAP particles are subject to swelling and can therefore form a gel with the adjacent swollen SAP particles. Said gel formation, often referred to as the gel-blocking effect, can block the liquid transmission towards the inner portion of the absorbent core. As a consequence, gel blocking can lead to potential liquid leakage and/or to re-wetting issues. To prevent gel blocking and to improve the fluid absorbent capacity of the absorbent core, individual SAP particles have to be sufficiently distant from one another, i.e. leaving voids between them.

This is generally obtained by mixing the SAP particles together with a cellulose-based fluff.

The trend to offer thinner absorbent articles involves using SAP particles as efficient as possible with less fluff as possible. Absorbent cores having a high SAP to fluff ratio is referred to as fluff-less or fluff free cores.

Examples of such fluff-less/free absorbent structures are disclosed in WO 2013/152809, where the absorbent core comprises less than 4 wt. % fluff.

One drawback of reducing the amount of fluff in absorbent articles is that when pressure is applied to the article, usually by body movements, the SAP particles are pressed and, the fluff liquid holding capacity being reduced, some liquid is refluxed into the surrounding layers, including towards the body. Humidity can therefore be transferred to the skin in an unpleasant rewet effect and can create side effects.

Because the absorbent core, having the main liquid retaining function of the article, is not as fast to acquire liquids as the ADL, the appropriate combination of these two elements are of utmost importance.

With regard to the currently known disposable absorbent articles or garments, there is a continuous need in the art to improve their liquid holding capacity and the distribution of liquid once acquired, and to decrease the liquid inlet time and the re-wetting effect. There is also a need for achieving these goals without requiring more expensive, chemically sophisticated, SAP particles, while maintaining the thinness of the articles. There is also a need for providing improved disposable absorbent articles or garments without increasing the complexity and cost of manufacture thereof.

SUMMARY OF THE INVENTION

The above goals, and other advantages, are achieved by the present invention.

To this end, the invention concerns a multilayer acquisition and distribution sheet nonwoven material for hygiene articles comprising at least three layers on top of each other:
- the first layer for acquiring and transferring body fluids to the second layer;
- the second layer for receiving the body fluids from the first layer and spreading the body fluids over this second layer, and
- the third layer comprising superabsorbent polymer (SAP) particles, for receiving the body fluids from the second layer, the second layer forwarding the body fluids to the third layer irreversibly.

The multilayer nonwoven material of the invention thereby acts as a core.

The invention thereby ensures that the body fluids can penetrate from to first layer, which acts as an acquisition layer, up to the third layer, the second nonwoven layer serving to decrease the fluid volume per surface unit, as a conventional dispersion layer. However the second layer of the invention additionally acts like a non-return valve, preventing, or at least strongly limiting, any fluid transfer from the third layer to the first layer.

By irreversibly, one should here understand that the SAP fluid uptake in the third layer combined with the structure of the second layer prevents most of the fluid to move back from the third layer into the second layer in reasonable conditions of use, with a rewet of 7 g or less, as measured according to EDANA WSP 70.3.R3 (acquisition time—ST) and WSP 80.10 (rewet—WB), preferably of 2 g or less and more preferably of 1 g or less.

The SAP particles are here dispersed in a nonwoven layer material, and not in fluff, as in absorbent core.

To irreversibly forward the body fluids to the third layer, the second layer is arranged with void volumes smaller than the void volumes of the third layer of which the fibers are coarse fibers (around >7 dtex), whereas those of the second layer are finer.

Ideally, the void volumes in the second layer may be smaller than the volumes of the SAP particles, at least in their swollen form, to prevent the SAP particles from migrating from the third layer to the second layer. The difference in void volumes, or void volume gradient, enables to create a pressure gradient slowing down fluid reflux from the third layer back to the second layer.

Additionally, as an acquisition layer, the first layer must intake body fluids rapidly. This requires that void volumes in the first layer are large enough and in particular larger than the void volumes in the second layer.

The multilayer acquisition and distribution sheet material of the invention is therefore inventive as it combines several effects to improve the capacities of an ADL layer:

an improved suction effect produced by the SAP particles creating a liquid intake gradient between the first and the third layer, and by avoiding gel blocking via SAP positioning, and An improved non-return effect between the third and second layers, produced by the difference in void volumes between these two layers.

The void volumes are related to the space between the fibers, which are bound together at multiple points, thereby forming an array presenting cavities, or voids. The void volume in a nonwoven material is a parameter well known to the person skilled in the art, and corresponds to all space available in a material which is not filled by material, like fibers and SAP. Calculation and measurement can be made by PMI porosimetry or air permeability. Preferably, the void volume, measured via air permeability at 100 Pa-20 cm$^2$, corresponds to an air permeability of between 1000 l/m$^2$/s and 12,000 l/m$^2$/s, still preferably between 2000 l/m$^2$/s and 3000 l/m$^2$/s.

The multilayer acquisition and distribution sheet material of the invention integrating SAP particles allows to at least partially perform the function of the absorbent core usually found in absorbing hygiene products. As a consequence, integrating such an ADL/core in a hygiene article improves the absorbing and retaining capacity of the article, and/or enables to make use of a thinner or fluff-free absorbent core.

In this later case, the multilayer sheet material of the invention functions both as an acquisition and distribution layer and an absorbent layer. The multilayer sheet material of the invention could therefore be directly sandwiched between the permeable top-sheet and the impermeable back-sheet.

In a particular embodiment, the SAP particles are dispersed in the third layer according to a pattern leaving channels, extending through the third layer from the second layer, free of SAP particles. A channel designates any kind of area of the layer, devoid of SAP over its thickness.

The channels where no SAP particles are dispersed, extending throughout the thickness of the third layer, enable to increase the absorbing efficiency of the third layer. Indeed, through the channels, the body fluids are able to penetrate faster deep into this layer and be absorbed by more SAP particles. This enables to increase the absorbing speed of this layer by increasing the path of the body fluids inside the third layer. This also has a beneficial effect against gel blocking, as the fluids can be distributed even to the deeper SAP particles.

In another embodiment, which can be combined with the previous embodiment, at least one layer can comprise continuous void spaces. By continuous voids spaces, it is referred to spaces devoid of nonwoven material. These continuous void spaces are a different concept from the void volume measured between the fibers in a nonwoven layer, but rather refer to cuts or holes of much larger size in a nonwoven layer. Such spaces can be arranged over the whole thickness of the layer, which is for example the case when pieces of nonwoven are cut and rearranged as will be described below, or over only part of the thickness of the layer, which is for example the case when one or more layers are submitted to a welding process.

The invention also relates to a process for dispersing SAP particles in the third layer of the multilayer nonwoven sheet material of the invention, comprising the steps of:

depositing SAP particles onto at least a part of the surface of the third layer, and impregnating the SAP particle into the third layer.

For the particular embodiment where the SAP particles are dispersed in the third layer according to a pattern leaving channels, extending through the third layer from the second layer, free of SAP particles, the process of the invention can comprise at least one of the steps of applying a mask on the surface of the third layer before deposition of the SAP particles;

welding at least the third layer;

cutting the third layer into pieces and adhering the pieces onto the second layer separated from each other.

For the particular embodiment where at least one layer comprises continuous void spaces, the process of the invention can comprise at least one of the steps of cutting at least one of the layers into pieces and adhering the pieces onto an adjacent layer separated from each other;

welding at least one layer.

Impregnating designates the action to make the SAP particles move from the surface into the nonwoven layer, within voids, in order to distribute the particle over at least part of the thickness of the layer.

Welding is a well-known step to a person skilled in the art and describes the action of pressing the nonwoven on a discrete area while applying heat, in order to compress irreversibly the nonwoven on this particular area.

The invention will be better understood with the following description of several examples, referring to the accompanying drawing on which:

5

Figure 1:
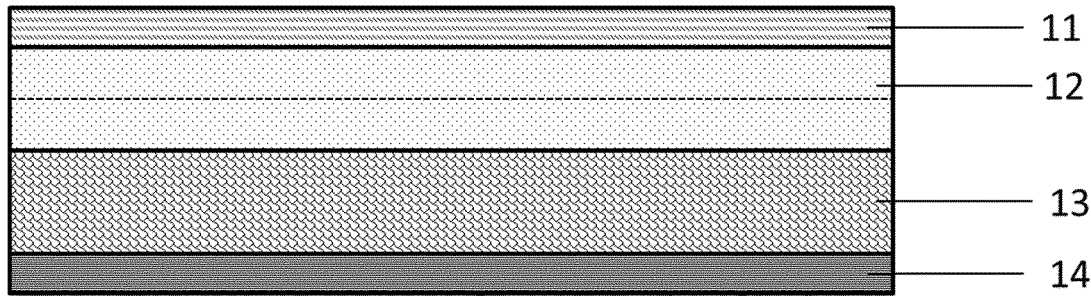
FIG. 1 is a sectional scheme of a conventional disposable absorbent article or garment.
Figure 2:
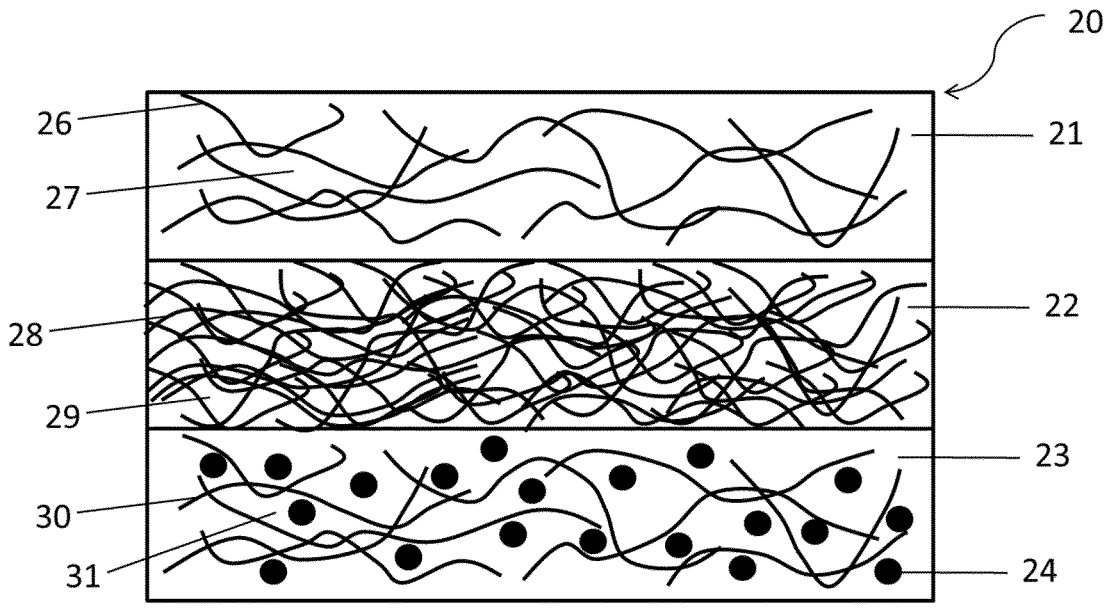
FIG. 2 is a sectional scheme of a multilayer acquisition and dispersion sheet material according to the invention.
Figure 3:
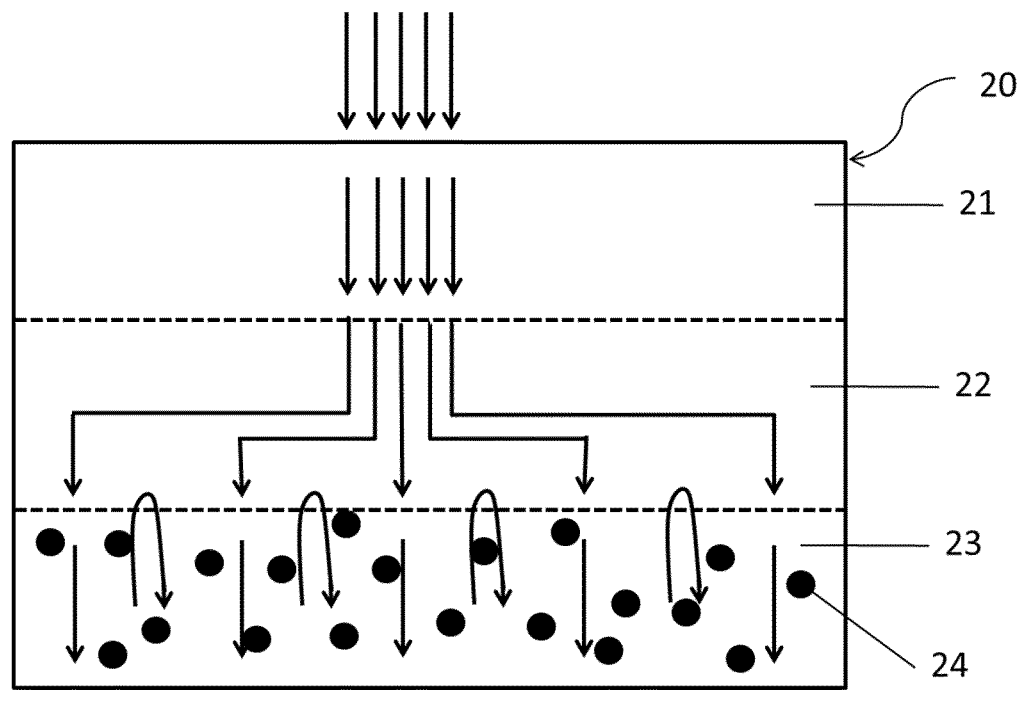
FIG. 3 illustrates body fluids flows in the material sheet of FIG. 2.
Figure 5:
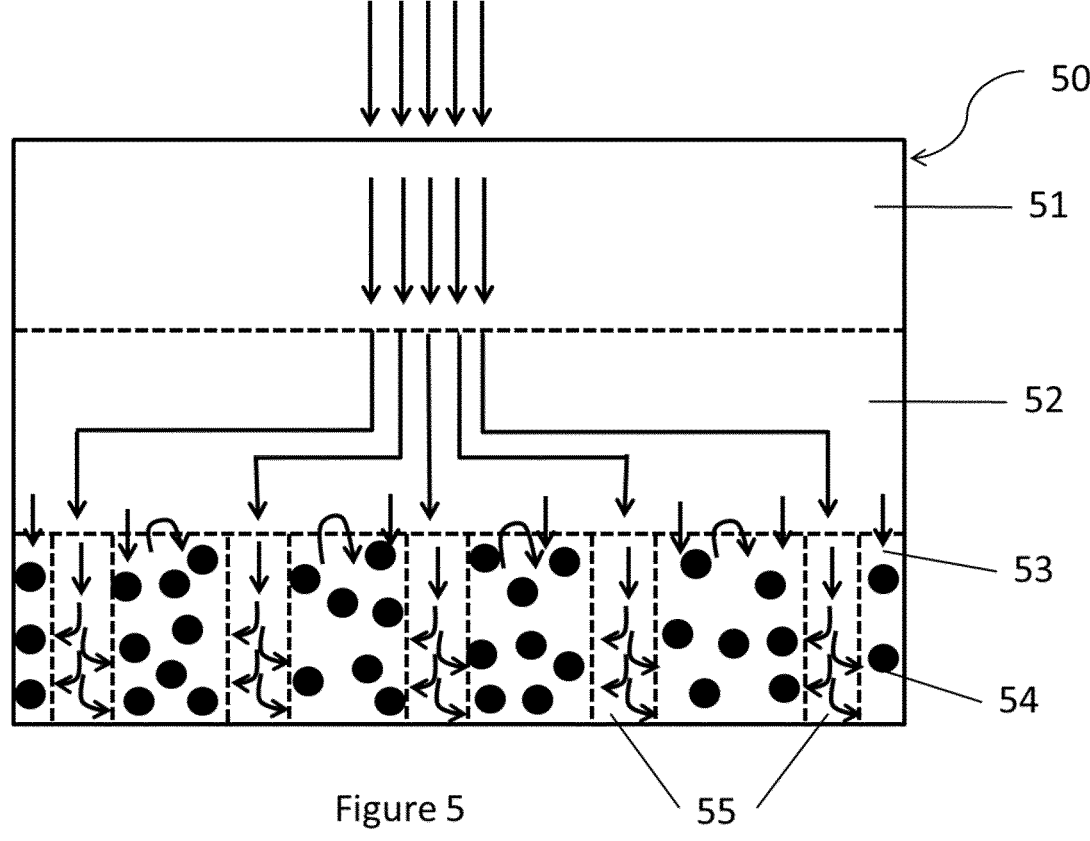
Figure 6A:
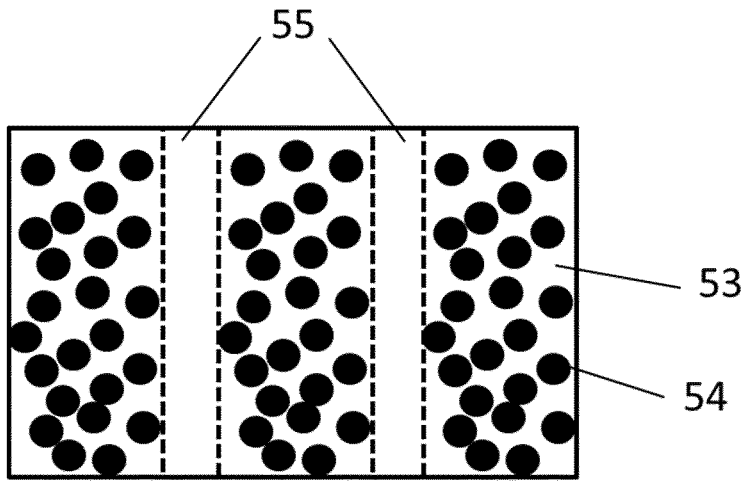
Figure 6B:
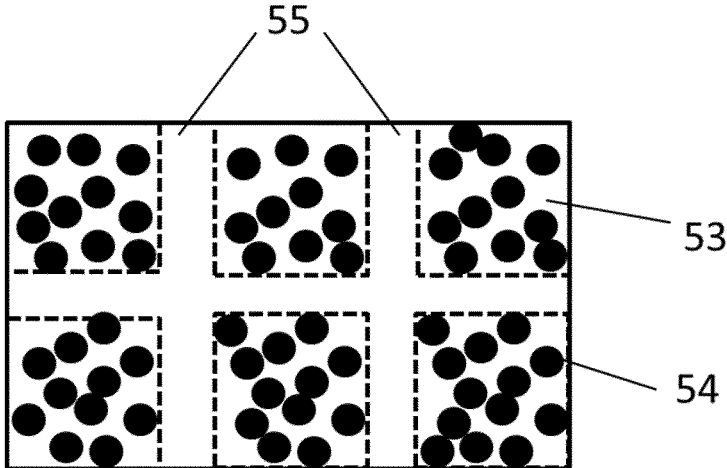
Figure 6C:
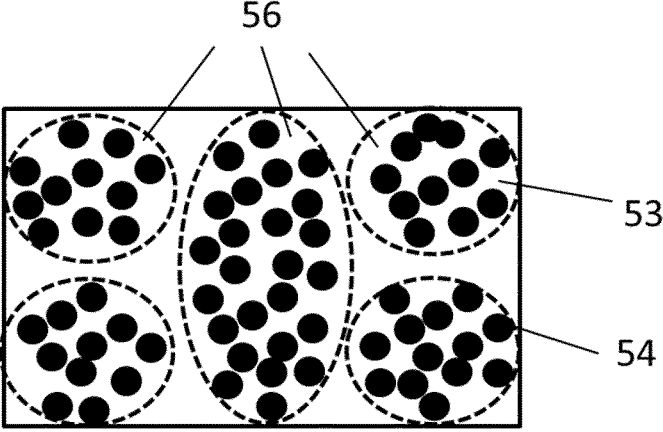
Figure 7:
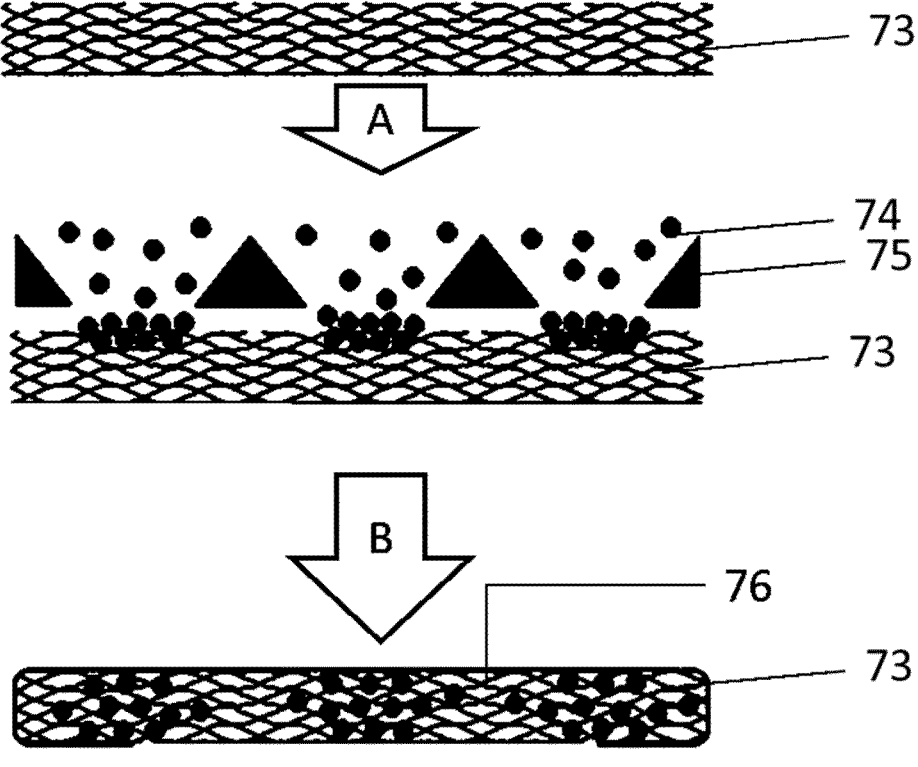
Figure 8:
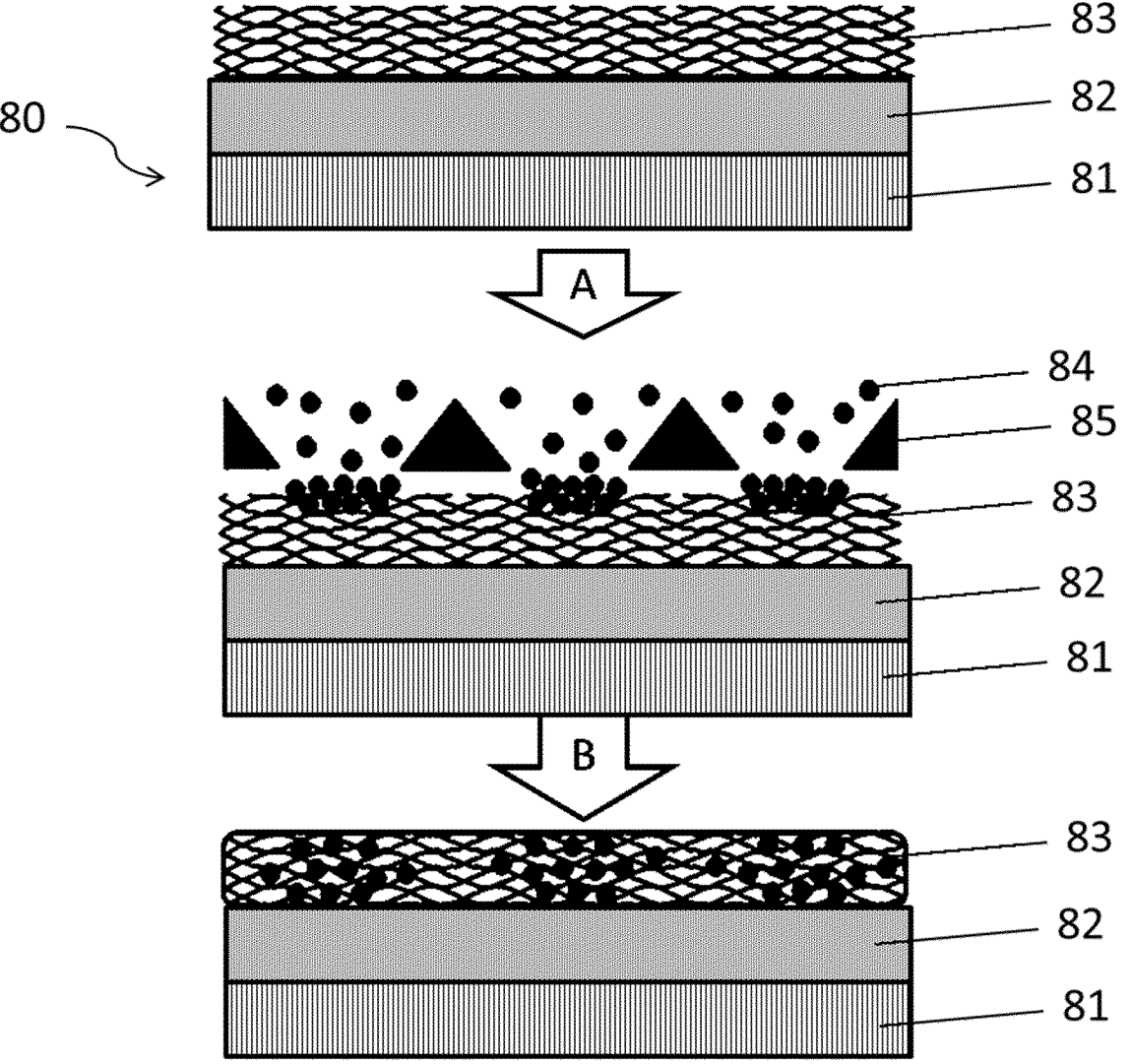
Figure 9:
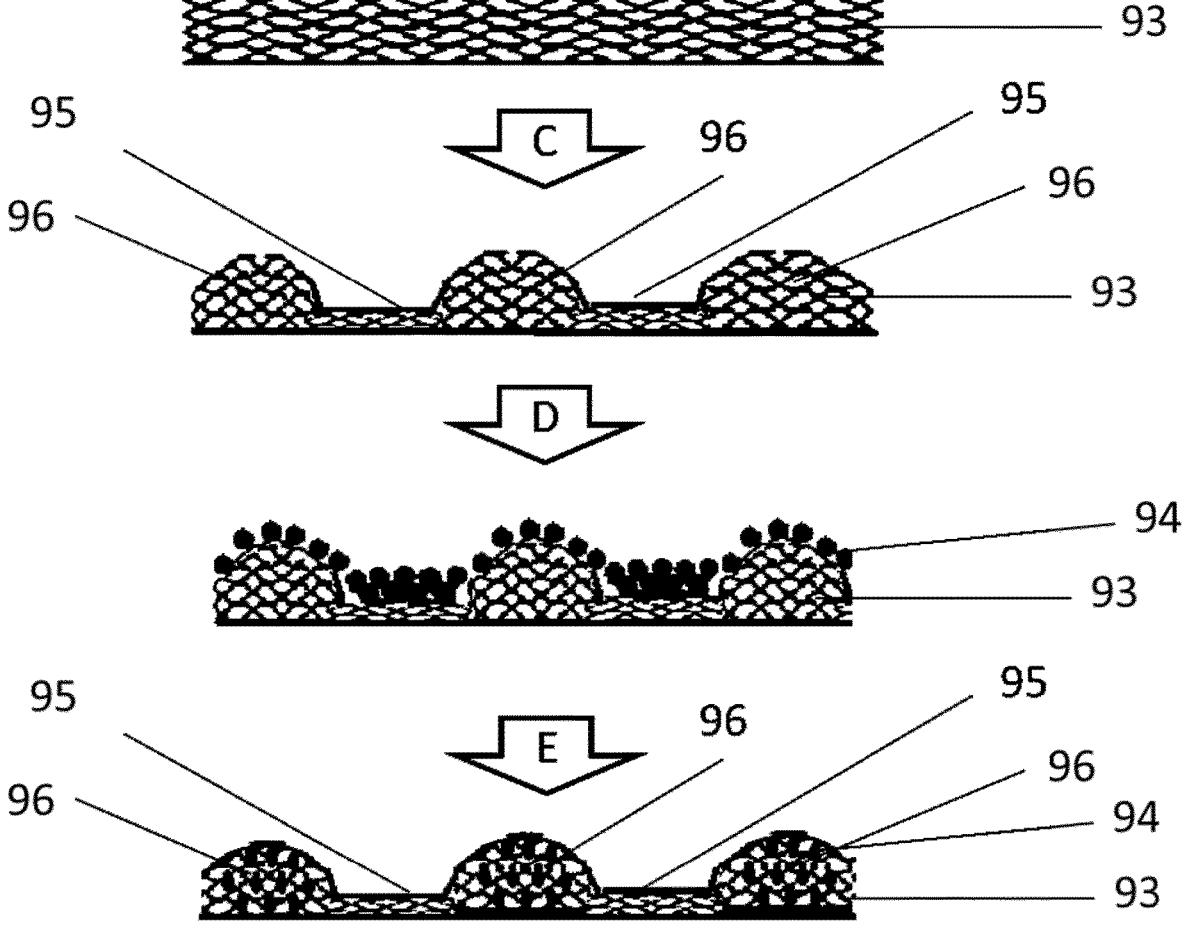
Figure 10:
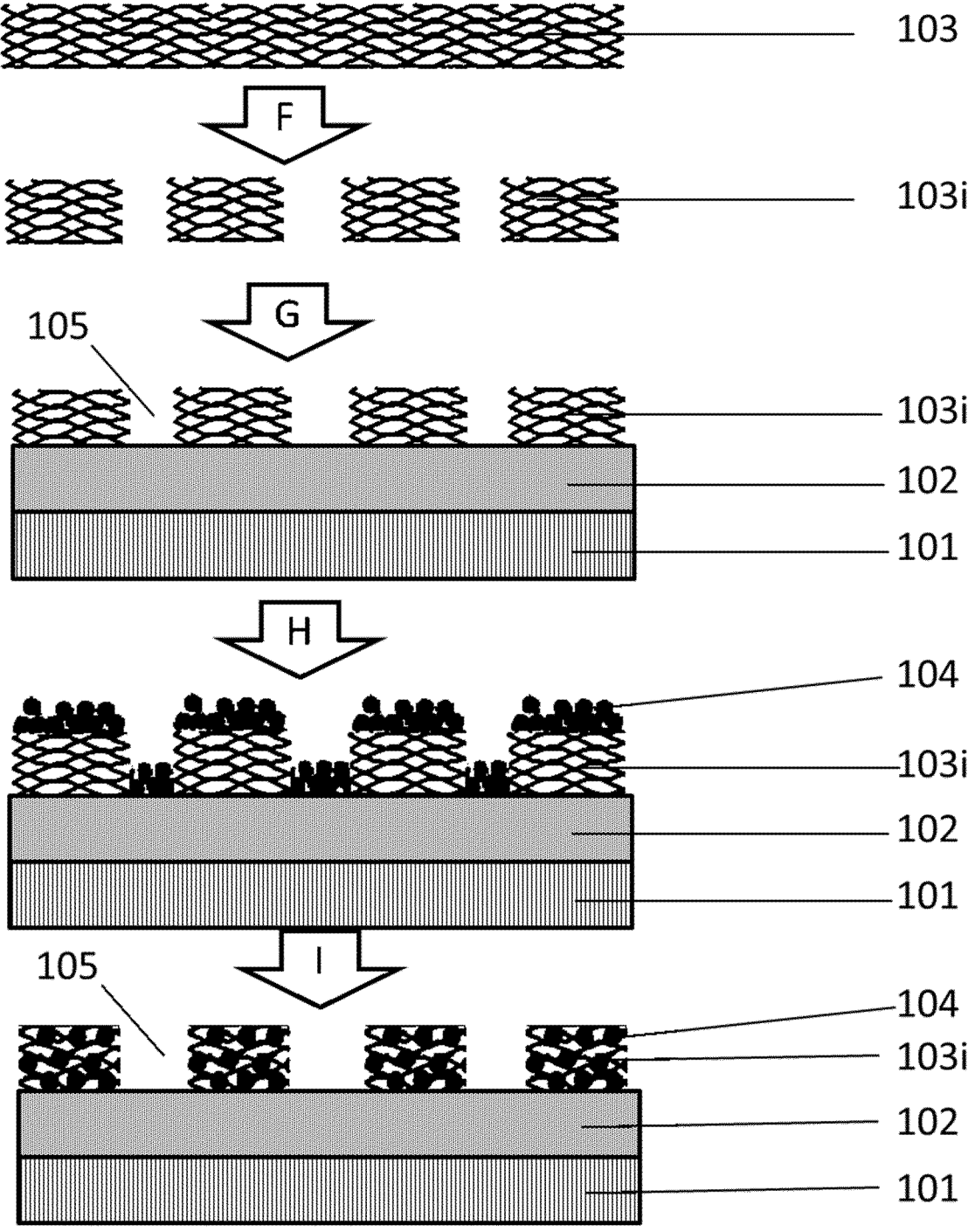
Figure 11:
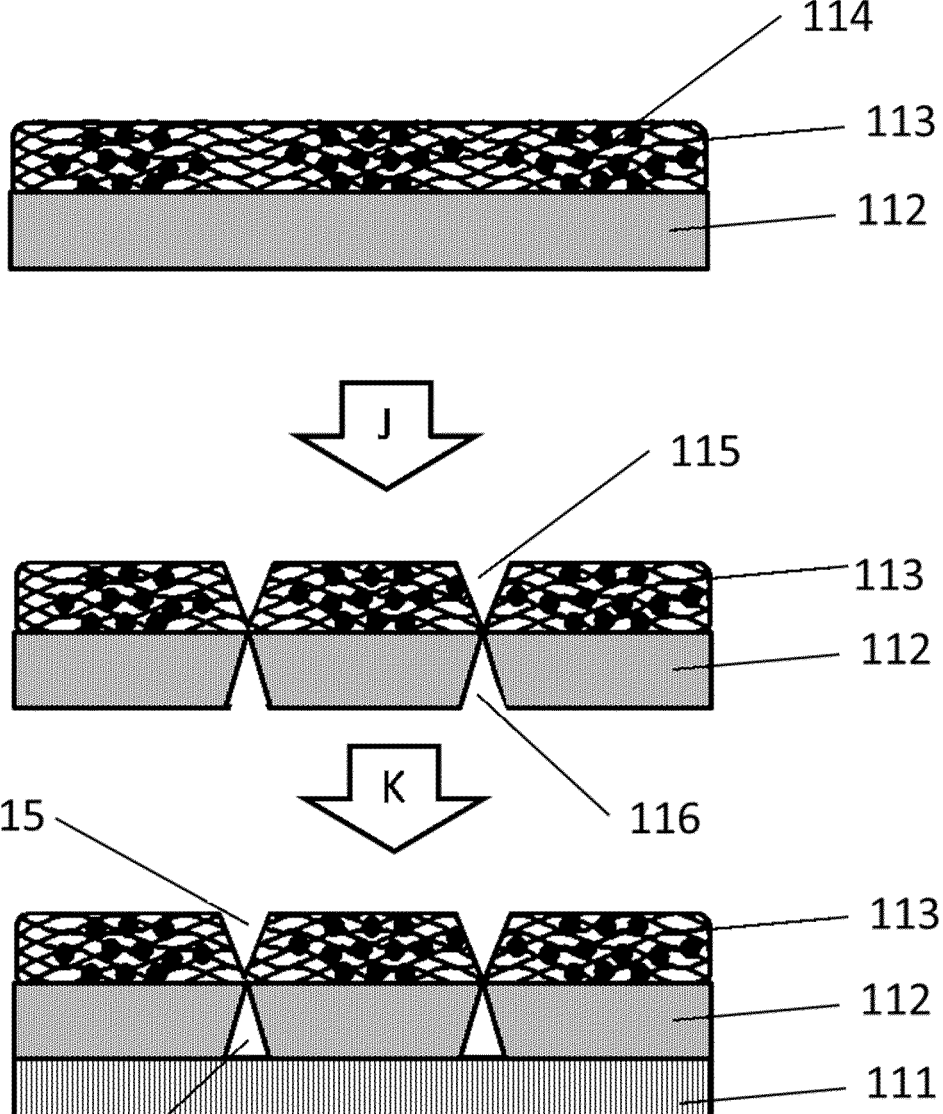
Figure 12:
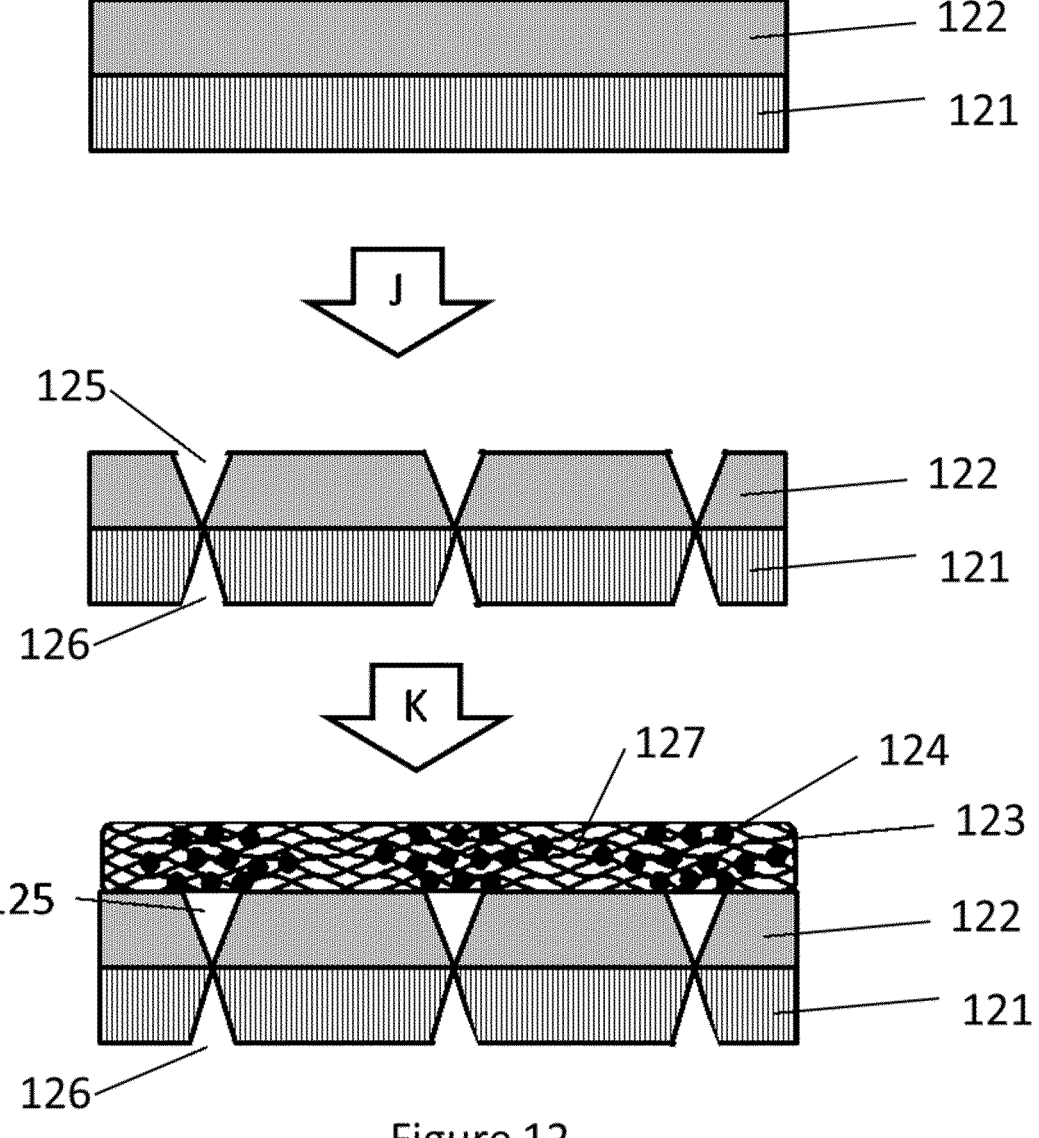

FIG. 5 is a sectional scheme of another multilayer acquisition and dispersion sheet material according to the invention;

FIGS. 6a, 6b and 6c are illustrative views from above of channel patterns in the third layer, according to the invention;

FIG. 7 is a scheme of the process of the invention;

FIG. 8 is a scheme representing another embodiment of the process of the invention;

FIG. 9 illustrates another embodiment of the process of the invention;

FIG. 10 illustrates still another embodiment of the process of the invention;

FIG. 11 illustrates another mode of preparation of the multilayer acquisition and distribution sheet nonwoven material of the invention, and FIG. 12 illustrates a further mode of preparation of the multilayer acquisition and distribution sheet nonwoven material of the invention, Referring to FIGS. 2 and 3, a multilayer acquisition and distribution sheet material 20 for hygiene articles comprises, on top of each other, a first layer 21, a second layer 22 and a third layer 23 comprising superabsorbent polymer (SAP) particles 24.

The first layer 21 comprises fibers 26, preferably coarse fibers, bound together so as so form voids 27.

The second layer 22 is made of fine hydrophilic fibers 28, which are more densely packed than the coarse fibers of the first layer 21. The fine fibers 28 are bound together so as to form voids 29.

The third layer 23 comprises coarse fibers 30, preferably rather hydrophilic, bound together so as so form voids 31. Some SAP particles 24 are dispersed within the third layer 23, within the voids 31.

The first and third layers 21 and 23 are porous layers, wherein porous according to the invention is defined by a void volume ranging from about 300 to about 500 cm³ of void volume/m², whereas the second layer 22 is composed of very fine hydrophilic fibers, ranging from 0.7 to 30 dtex and preferably from 1.5 to 7 dtex, resulting in small voids and thereby preventing liquid from going back to the surface, and also limiting the possibility for the SAP particles to migrate therein.

Fibers suitable for the various layers 21, 22, 23 are well known to the person skilled in the art and can be of any suitable material or blend of materials known to a person skilled in the art in the field of nonwoven materials. For example, they can be, but not limited to, polymeric synthetic fibers consisting of polyethylene terephthalate (PET), polyethylene (PE), polypropylene (PP), copolymers of ethylene and propylene (COP), PET/PE, PET/PP, PET/COP, PP/PE, PET/COPET, polyacrylic acid (PLA), PLA/PP, polyvinylalcohol, viscose.

In the first layer 21, the fibers preferably have a titer of between 2 and 28 dtex.

In the second layer 22, the fibers have a lower titer than the fibers in the first layer, and preferably a titer comprised between 0 and 7 dtex, in order to confer to the second layer a high liquid holding and distribution capacity, allowing the SAP particles of the layer beneath slowly take up the liquid thereby avoiding any gel blocking. The fibers in the second layer are preferably hydrophilic, either intrinsically or by hydrophilic coating or treatment.

Fibers suitable for the third layer 23 have a higher titer than in the second layer, which is preferably comprised between 2 and 70 dtex.

The void volumes in a specific layer, for example in the first and/or the third layer, can be modified by a heat treatment, as known to the person skilled in the art.

In practice, as illustrated by the arrows on FIG. 3, body fluids, like for example urine or blood, penetrate in the first layer 21, over a limited area. The first layer 21 can rapidly acquire the fluids and transfer them to the second layer 22.

Due to its smaller fibers size, small void volumes and hydrophilicity, the body fluids penetrate and migrate, by capillarity, in all directions of the layer 22, thereby "spreading" the body fluids over a larger area of the material sheet.

The body fluids are then forwarded from the second layer 22 to the third layer 23 where they are absorbed by the SAP particles 24, thereby creating a suction effect ensuring the flow direction, i.e. from the first layer 21 towards the third layer 23. Additionally, as the void 29 volumes in the second layer 22 are smaller than the voids 31 in the third layer 23, thereby creating a counter-pressure impacting the speed at which the body fluids can return into the second layer 22 after having penetrated into the third layer 23, thereby leaving time to the SAP particles to fully absorb the fluids. Even if some body fluids reflux into the second layer 22, the difference in hydrophilicity between the first and the second layers 21 and 22 further prevents body fluids from refluxing into the first layer 21, hence the comparison with a non-return valve.

Figure 4:
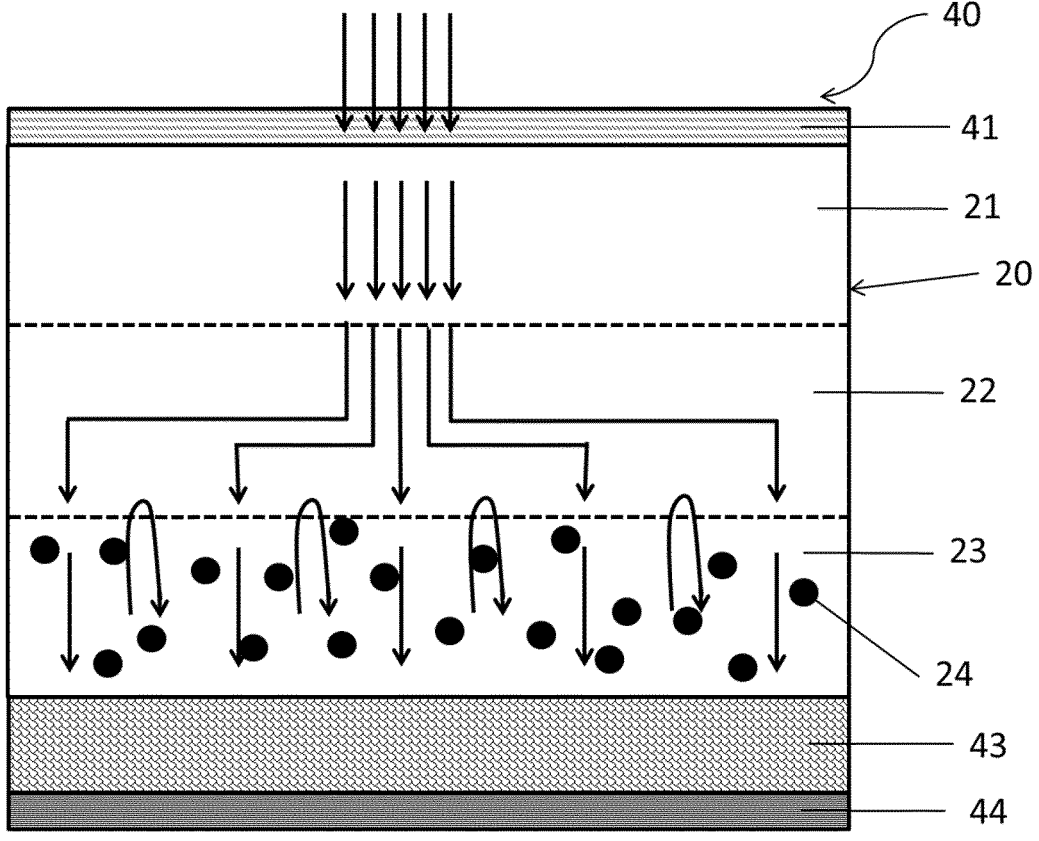
FIG. 4 illustrates the material sheet of FIGS. 1 and 2 incorporated in an hygiene absorbent article.

As illustrated on FIG. 4, the multilayer material sheet 20 of the invention can be used as ADL in an absorbent article 40, for example a diaper, sanitary towel or wounddressing. A permeable top sheet 41 is applied onto the first layer 21, for example to give a soft touch feeling to the article on its body side. An impermeable back-sheet 44 is applied at the opposite side, to ensure that no humidity can be further transferred. Optionally, an absorbent core 43 can be sandwiched between the ADL 20 and the back-sheet 44. This absorbent core is optional and its presence may depend on the intended use of the article. It is for example made of fluff wherein SAP particles are dispersed, in articles intended to absorb and retain large influxes of liquids, like diapers, or a paper layer. The amount of fluff can be for example reduced for some feminine hygiene article supposed to deal with smaller amount of body fluids.

Alternatively, in particular for wound dressing, the third layer can be the layer intended to be closer to the body.

Three layers have been so far described but the multilayer sheet material of the invention can comprise more than three layers, for example to combine physical properties from different nonwoven materials or fibers. These additional layers could for example display a decreasing void volumes and/or increasing hydrophilicity, to create an actual gradient of void volumes and/or hydrophilicity.

Similarly, one or more additional dispersion layers could be added, in contact with one side or the other of the second layer; one or more additional coarse fibers layers could be added between the second and the third layer, possibly comprising SAP particles dispersed therein. One could imagine that SAP having different properties, like swelling capacity or size, could be dispersed in different nonwoven layers.

For some applications, the absorbent core is absent from the article. The absorbing and retaining power of the third layer 23, wherein SAP particles are dispersed, is sufficient in itself.

In such cases, it can be interesting to slightly increase the thickness and/or the SAP particles load of the third layer to increase it absorbing and retaining capacity.

However, increasing the thickness and/or the SAP particles load of the third layer can lead to unwanted gel-blocking effect, as discussed earlier.

In order to prevent this effect, channels free of SAP particles are advantageously patterned in the third nonwoven layer.

Referring to FIG. 5, a multilayer acquisition and distribution sheet material 50 according to the invention comprises a first layer 51 for acquiring and transferring body fluids and a second layer 52 for receiving the body fluids from the first layer and spreading the body fluids over this second layer, similar to the layers 21 and 22 described above. A third layer 53 comprises superabsorbent polymer (SAP) particles 54, for receiving the body fluids from the second layer. The SAP particles 54 are not evenly distributed within third layer 53, but are distributed according to a pattern, leaving some areas free of particles, over the whole thickness of the layer, thereby forming channels 55.

As illustrated by the arrows of FIG. 5, body fluids are transferred from the second layer 52 to the third layer 53 over most of the interface area. When penetrating into the third layer onto areas containing SAP particles, the body fluids are first absorbed by the SAP particles close to the layer interface. When penetrated into the third layer 53 onto areas free of SAP particles, i.e. into the channels, the body fluids are able to follow the channels and penetrate into the SAP containing zones at a deeper level.

This way, not only the SAP particles close to the interface between the second and third layers 52 and 53 are able to absorb body fluids, but also the deeper particles. Without the channels, the body fluids would first reach the SAP particles close to the interface, which would in turn become swollen, and then have to find a path between the swollen SAP particles, to reach deeper absorbing SAP particles. The channels 55 thereby allow to improve the absorbing potential of the layer, along with the uptake time, and enable increasing the thickness of the third layer while still preventing the gel blocking effect and making optimal use of the SAP particles.

The channels 55 can have any suitable shape and are generally not cylindrical. Seen from above, the channels can, for example, have the shape of stripes, as illustrated on FIG. 6a, extending throughout the area of the layer, or the shape of grid as illustrated on FIG. 6b, or the SAP particles 54 can be grouped in islands as illustrated on FIG. 6c. Any other suitable arrangement of the channels and SAP particles is possible, as long as a path is created, for the body fluids, throughout the thickness of the third layer 53.

The shape of the channels and the zones containing SAP particles may depend on the process used to apply/disperse the SAP particles in the third layer.

We will now describe the process to prepare the multilayer acquisition and distribution sheet material of the invention.

The technologies commonly used to prepare nonwoven layers are applicable to the process of the invention.

The multilayer sheet material of the invention can be made, for example, by preparing the three layers separately and then assembling them together, by welding or gluing, as known to the person skilled in the art.

It can also be made by preparing several carded webs, each web comprising a specific type of fibers or blend of fibers, overlapping the webs and then bonding the fibers together, thereby creating a multilayer nonwoven in one bonding step, for example by thermo-bonding. Alternatively, part of the layers can be prepared from carded webs bonded together into a nonwoven, which is then assembled to another layer by welding or gluing.

In the multilayer of the present invention, the challenge is to apply the SAP particle into the third layer, either in a homogeneous manner or according to a pattern.

To this purpose, SAP particles can be impregnated into the third layer using techniques commonly used to impregnate powder form materials into porous structures (textiles, nonwovens, papers, foams . . . ), like for example Fibroline technology or classical wet impregnation techniques. The SAP particles can be applied onto the third layer of the multilayer sheet material already manufactured or on an isolated nonwoven layer, which will then be assembled with the other layers to form the material sheet of the invention. This last option is however less efficient, as more manufacturing steps are needed.

Referring to FIG. 7, in a step A, SAP particles 74 are applied onto the surface of a nonwoven layer 73, corresponding to the third layer of the invention. The particles 74 are here applied according to a specific pattern, owing to a mask 75, hiding from the deposition mechanism, the area corresponding to the expected channels 76. Deposition of the particles can be performed by any suitable mechanism, like for example powder scattering. For a homogeneous dispersion of particles, no mask is used.

In a step B, the nonwoven layer 73, covered with SAP particles 74 is subjected to the impregnation step, using for example vibrations and/or electric field in order to let the particles penetrate down throughout the whole thickness of the layer 73.

This layer 73 can then be assembled, i.e. glued or welded, to the other layers of the multilayer sheet material of the invention.

Alternatively, referring to FIG. 8, the SAP particles 84 can be applied to the third layer 83 of a multilayer sheet material 80, also comprising a first layer 81 and a second layer 82. The void volumes in the second nonwoven layer 82, according to the invention, are small enough to create a barrier which will prevent most of the particles 84, applied here using a mask 85, from impregnating the material beyond the third layer 83.

The masks 75 or 85 described above allows selectively dosing or depositing SAP particles onto discrete areas, not connected between them, allowing upon impregnation to pattern the channels free of SAP between the SAP containing zones. Other techniques are applicable to reach a similar result.

For example, with reference to FIG. 9, a third layer 93 can be welded, in a step C, according to a specific pattern. Welding involves applying a pressure and heat to discrete areas 95 of the nonwoven, such that, upon release of the pressure, the nonwoven, in these areas, remains compacted. This means that, in areas 95, the fibers have come close to each other, the resiliency of the fibers connecting points is, at least partially, lost and the voids in these portions of the nonwoven are consequently reduced. The areas 96, where no or moderate pressure has been applied, remain soft with resiliency and voids globally unaltered. Optionally, a relofting step, like for example thermal relofting, can be applied to ensure that the non-embossed areas 96 recover their full properties.

In a step D, SAP particles 94 can then be applied to the full surface of the layer 93, or alternatively could be selectively deposited.

The layer 93, in a step E, can be submitted to an impregnation step, for example using the Fibroline technology. The voids in the embossed portions 95 being too small to accommodate SAP particles, this creates a barrier and the particles 94 migrate to the non-embossed areas 96, thereby creating a pattern of distribution of the SAP particles 94.

SAP particles which may remain at the surface of the welded areas 95 can be removed using various techniques, such as, for example, air blowing, aspiration or by brushing.

Referring to FIG. 11, continuous void spaces 115 and 116 can be formed by welding, in a step J a nonwoven sheet comprising a third layer 113 in which SAP particles are dispersed (here disclosed dispersed according to a pattern) and a second layer 112. The assembled layers 112 and 113 are submitted to hot pressing on both surfaces resulting in the formation of void spaces 115 and 116 in both materials with condensed fibers at the interface of the two layers 112 and 113.

In a step K, the welded layers 112 and 113 can then be assembled to a first layer 111 thereby forming, in this case a nonwoven sheet material comprising channels in the third layer and continuous void spaces in the second and the third layer. In the particular case of FIG. 11, in the third layer 113, the channels and the continuous void spaces 115 overlap, but this may not necessarily be the case. This configuration can be particularly interesting for wound dressing. In this case, the third layer can be the layer closer to the body member, i.e. in an opposite configuration compared to other products like diapers.

The same steps J and K may be applied to other layers, as disclosed on FIG. 12. A first layer 121 and a second layer 122 assembled thereto, are welded to create continuous void spaces 125 and 126, in both layers respectively. A third layer 123, wherein SAP particles 124 are distributed according to a pattern so as to leave channels 127 free of SAP particles, is then added onto the second layer 122. In this case, the continuous void spaces 125 and 126 are not located so as to overlap the channels 127. This configuration can enable part of body fluids incoming the first layer to rapidly reach the SAP particles in the third layer through the continuous void spaces, while some of the fluid will take a longer path through the layers 121 and 122 and the channels 127 to reach deeper SAP particles 124. This can enable to deal with short but intense influx of fluids in the material.

Another technique to create channels free of SAP particles in the third layer is to mechanically cut the third layer into pieces and to adhere the pieces onto the second layer separated from each other. With reference to FIG. 10, an isolated nonwoven layer 103, suitable to serve as the third layer of the invention, is cut into pieces 103i, in step F.

The pieces can have any suitable shape, depending on the final use of the ADL of the invention. They can, for example, be squares, rectangles or stripes.

In step G, the pieces 103i are adhered to the second layer 102 of the invention, by any suitable technique known by the person skilled in the art, for example using glue or welding. The pieces 103i are positioned so as to leave a gap between them. The first layer 101 of the invention is here also represented. The first nonwoven layer 101, the second layer 102 and the pieces of third layer 103i represent the structure of the multilayer sheet material of the invention. Though the third layer is not here a continuous nonwoven layer, the gaps in between the layers are relatively small. The nonwoven material represents more than 50% of the total surface of the third layer, preferably more than 75% of the surface of the third layer, and therefore fall under the appellation "nonwoven layer" as encompassed by the claimed invention.

In step H, SAP particles 104 are deposited onto the surface of the material sheet. The deposition illustrated here is non selective, SAP particles accumulate both in the gaps and on the pieces 103i of third layer.

It could however be foreseen that a mask is used to deposit selectively the particles onto the nonwoven pieces 103i. In step I, the SAP particles 104 are impregnated into the nonwoven pieces 103i, using for example the Fibroline technology, or any other suitable technology.

Both the SAP particle 104 distributed on top of the pieces 103i and in the gaps in between are impregnated into the pieces 103i, leaving the gaps or channels 105 between the pieces 103i free of SAP particles.

Several other configurations are foreseeable, depending on the final use. Any combination of the following can be prepared:

a continuous or discrete distribution of SAP in the third layer, forming channels in the latter case;
   no continuous void spaces or continuous voids spaces in anyone or more than one of the three layers;
   in the case continuous void spaces and channels are present, they can be aligned or not;
   the continuous void spaces may be obtained by welding or by mechanical cutting and placing of layer(s) pieces.

Additional layers, like for example, but not limited to, a top sheet, an absorbent core, a boosting layer or impermeable sheet, can be added either on top of the first layer or below the third layer. The terms "on top" and "below" being here to describe a relative position, independently of any absolute position. In any case, the second layer is in direct contact with both the first and third layer, no other fibrous layer may be inserted in between.

SAP particles or any fiber of the nonwoven sheet material can be treated for odor control. SAP particles may comprise various types of SAP particles in order to mix various properties.

In general, the amount of SAP particles can vary between 20 gsm and 450 gsm, preferably between 30 gsm and 80 gsm for femcare applications and between 200 gsm and 400 gsm for baby and incontinence applications. • The SAP can be—but not limited to—Ekotec, Sumitomo, BASF, SDP and depends on the application.

The temperature used for changing the void volume (for example for embossing or relofting) can vary between 30° C. and 180° C., but is preferably between 70° C. and 130° C.

An example of composition and preparation of a Multi-layer acquisition and distribution nonwoven sheet material of the invention is described below.

EXAMPLE

A triple-layer acquisition and distribution sheet nonwoven material (ADL) of 150 gsm, for hygiene articles, is prepared with a first layer corresponding to 25% of the weight (37.5 gsm) and consisting in a blend of PET and PET/coPET fibers having a titer between 2 dtex and 28 dtex;
   a second layer corresponding to 25% of the weight (37.5 gsm) and consisting in a blend of PET and PET/coPET fibers having a titer between 0 dtex and 7 dtex, and
   the third layer corresponding to 50% of the weight (75 gsm) and consisting in a blend of PET and PET/coPET fibers having a titer between 2 dtex and 28 dtex.

The first layer corresponds to the side of the material intended to be the bodyside.

The ADL has a measured air permeability of 2500±500 l/m²/s.

In EDANA assay WSP 70.3.R3, the sample has a strike-through (ST) time of 0.59 s.

In EDANA assay WSP 80.10, the sample has a wetback (WT) of 0.09 g.

400 gsm (gram per square meter) of SAP particles are applied onto the exposed areas of the third layer, impregnation is done using a Fibroline module with flat electrodes at a speed of 20 m/min. After impregnation, the ADL is wrapped with a core wrap material, here a SMS of 9 gsm.

Two samples were prepared, each having a size of 40 cm×10 cm. In a first sample, SAP are applied to the whole surface of the ADL, for control. In a second sample, SAP are applied according to a pattern as in FIG. 6a, owing to a mask, leaving a band of 1 cm in the middle of the sample, free of SAP. The second sample therefore has overall 10% less SAP than the first sample (control sample), 10% of its area being devoid of SAP particles.

The two samples were tested comparatively according to an internal TWE test method based on the Hytec test. 4×70 ml synthetic urine (saline solution 0.9% NaCl) was dosed, with a waiting time of 5 minutes between the doses. The acquisition time for every dose is measured with a chrono. After the fourth waiting time, the rewet is measured by placing some rewet papers of 19 cm×10 cm for 15 seconds on the samples and measuring the amount of liquid absorbed by the rewet papers. The loading during acquisition and rewet is 8 kg.

The inlet times after each dose and final rewet time are summarized in the table 1 below.

TABLE 1

|  | Sample 1 (control) | Sample 2 |
| --- | --- | --- |
| Dose 1 | 13.96 s | 13.24 s |
| Dose 2 | 35.86 s | 17.96 s |
| Dose 3 | 51.57 s | 16.14 s |
| Dose 4 | 55.39 s | 14.06 s |
| Rewet | 5.03 g | 3.65 g |

Owing to the channels, inlet time is maintained more or less constant dosing after dosing and urine retention is increased, thereby demonstrating the improvement brought by the SAP free channels in the ADL.

The invention claimed is:

1. A multilayer acquisition and distribution sheet nonwoven material for hygiene articles comprising at least three layers on top of each other:

a first layer for acquiring and transferring body fluids to the second layer;

a second layer for receiving the body fluids from the first layer and spreading the body fluids over the second layer, and a third layer comprising superabsorbent polymer (SAP) particles, for receiving the body fluids from the second layer, the second layer forwarding the body fluids to the third layer irreversibly, the second layer comprising void volumes and wherein the void volumes in the second layer are smaller than the SAP particles, wherein the second layer is arranged with the void volumes smaller than void volumes of the third layer of which the fibers are coarse fibers, whereas fibers of the second layer are finer, wherein void volumes in the first layer are larger than the void volumes in the second layer, wherein the SAP particles are dispersed in the third layer according to a pattern which leaves channels extending through the third layer from the second nonwoven layer, free of SAP particles, wherein the channels do not extend into the second layer or the first layer, wherein the first layer and the second layer comprise a plurality of discrete portions, with regions between the plurality of discrete portions each defining a continuous void space, wherein the continuous void spaces are located so as to not overlap with the channels in the third layer.

2. The multilayer acquisition and distribution sheet nonwoven material of claim 1, wherein the fibers of the second layer have a fiber size in a range of 0.7 to 7 decitex (dtex).

3. The multilayer acquisition and distribution sheet nonwoven material according to claim 1, wherein:

fibers of the first layer have a first fiber size in a first range of 2 to 28 dtex;

fibers of the second layer have a second fiber size in a second range of 0.7 to 7 dtex; and fibers of the third layer have a third fiber size in a third range of 2 to 70 dtex.

4. The multilayer acquisition and distribution sheet nonwoven material of claim 1, wherein the channels are free of SAP particles in a swollen state, where fluid is present in the third layer, and in a non-swollen state, where fluid is not present in the third layer.

* * * * *